US008649852B2

(12) United States Patent
Song et al.

(10) Patent No.: US 8,649,852 B2
(45) Date of Patent: Feb. 11, 2014

(54) METHOD OF SIGNAL ENHANCEMENT FOR ECG DEVICES

(75) Inventors: Zhendong Song, Medina, MN (US);
Sheng Wang, Maple Grove, MN (US)

(73) Assignee: Medtronic, Inc., Minneapolis, MN (US)

(\*) Notice: Subject to any disclaimer, the term of this patent is extended or adjusted under 35 U.S.C. 154(b) by 131 days.

(21) Appl. No.: 13/099,065

(22) Filed: May 2, 2011

(65) Prior Publication Data

US 2012/0283586 A1 Nov. 8, 2012

(51) Int. Cl.
*A61B 5/02* (2006.01)
*A61B 5/04* (2006.01)
*A61N 1/00* (2006.01)

(52) U.S. Cl.
USPC ............. 600/509; 600/374; 600/508; 607/18

(58) Field of Classification Search
USPC .......................... 600/509, 508, 374; 607/18
See application file for complete search history.

(56) References Cited

U.S. PATENT DOCUMENTS

| | | | |
|---|---|---|---|
| 4,223,678 A | 9/1980 | Langer | |
| 4,295,474 A | 10/1981 | Fischell | |
| 4,310,000 A | 1/1982 | Lindemans | |
| 4,313,443 A | 2/1982 | Frosch | |
| 4,365,639 A | 12/1982 | Goldreyer | |
| 4,593,702 A | 6/1986 | Kepski et al. | |
| 4,686,988 A | 8/1987 | Sholder | |
| 5,135,004 A | 8/1992 | Adams | |
| 5,331,966 A | 7/1994 | Bennett et al. | |
| 5,987,352 A | 11/1999 | Klein et al. | |
| 7,027,858 B2 | 4/2006 | Cao et al. | |
| 2006/0094972 A1 | 5/2006 | Drew | |
| 2006/0095091 A1 | 5/2006 | Drew | |
| 2006/0095092 A1 | 5/2006 | Drew | |
| 2006/0217777 A1 | 9/2006 | Strom et al. | |
| 2006/0235489 A1 | 10/2006 | Drew et al. | |
| 2008/0183087 A1 | 7/2008 | Song | |
| 2008/0243200 A1 | 10/2008 | Scinicariello | |
| 2009/0177073 A1* | 7/2009 | Sonnenborg | ................. 600/386 |
| 2010/0022902 A1 | 1/2010 | Lee et al. | |
| 2010/0312131 A1 | 12/2010 | Naware et al. | |

OTHER PUBLICATIONS

Burke, Martin C., et al., "Analysis of Electrocardiograms for Subcutaneous Monitors", Journal of Electrocardiology, 2003, pp. 227-231, vol. 36 Supplement.
Horacek, B. Milan et al., "Optimal Electrocardiographic Leads for Detecting Acute Myocardial Ischemia", Journal of Electrocardiology, 2001, pp. 97-111, vol. 34 Supplement.

(Continued)

*Primary Examiner* — Niketa Patel
*Assistant Examiner* — Lindsey G Hankins
(74) *Attorney, Agent, or Firm* — Reed A. Duthler; Stephen W. Bauer (57) ABSTRACT

An embodiment of the invention comprises a method of monitoring cardiac electrical activity with two or more ECG devices and computing an enhanced cardiac electrical signal from the cardiac electrical signals obtained from the two or more ECG devices. Electrodes of the two or more ECG devices are positioned in a manner to provide an electrical potential difference that is large enough to give useful information about a given ECG signal. The method further includes recommending addition of a supplemental ECG device when it is determined that the one or more of the existing ECG devices are inadequate for providing cardiac electrical data that identifies a specific cardiac event.

15 Claims, 6 Drawing Sheets

(56) References Cited

OTHER PUBLICATIONS

Lockyer, J. Norman, "The Geometric Interpretation of Monge's Differential Equation to all Conics", Nature, Oct. 25, 1888, pp. 619-621.
Song, Zhendong et al., "The Feasibility of ST-Segment Monitoring With a Subcutaneous Device", Journal of Electrocardiology 2004, ppgs. 174-179, vol. 37.
Song, Zhendong, "The Biploar Precordial Electrocardiogram Theory and Practice", Dec. 2005, 185 pgs. Department of Biomedical Engineering, College of the Illinois Institute of Technology.
Widman, Lawrence E., et al., "Electrocardiographic Body Surface Potential Maps of the QRS and T of Normal Young Men. Qualitative Description and Selected Quantifications", Journal of Electrocardiology, 1988, pp. 121-136, 21 (2).

* cited by examiner

METHOD OF SIGNAL ENHANCEMENT FOR ECG DEVICES

FIELD

The present invention relates to a method of providing enhanced cardiac electrical signals.

BACKGROUND

Devices for monitoring cardiac events (e.g., arrhythmia, myocardial infarction, etc.) and the cardiac electrical activity are well known in the art. These include external devices generally known as Electro-Cardiograms (ECG) wherein a plurality of electrodes are positioned at predetermined locations on a patient's body for monitoring the electrical waves corresponding to the various states of the heart. ECG devices that can be subcutaneously implanted in a patient are also well known and widely used.

Subcutaneous devices having integrated electrodes used for monitoring cardiac electrical activity are restricted in size to ensure that the electrodes are sufficiently spaced apart for providing an electrical potential difference that is large enough to give useful information about a given ECG signal. However, there is an ever increasing desire for miniaturization for ease of surgically implanting and/or replacing the device with minimally invasive procedures, and also for lending comfort to the patient after a device has been implanted. As can be appreciated, decreasing the size of a subcutaneous device also decreases the distance between the device's integrated electrodes. This then decreases the amplitude of the cardiac electrical signal measured by the electrodes, along with likely decreasing the signal-to-noise ratio.

SUMMARY

An embodiment of the invention comprises a method of monitoring cardiac electrical activity with at least two subcutaneous devices. The first of the two subcutaneous devices includes a first pair of electrodes wherein the first electrode of the first pair of electrodes is positioned near a location of maximum electrical potential (relative to the second electrode), and the second electrode of the first pair of electrodes is positioned along a first equipotential line extending from the location of maximum electrical potential. Similarly, the second of the two subcutaneous devices includes a second pair of electrodes wherein the first electrode of the second pair of electrodes is positioned near a location of minimum electrical potential (relative to the second electrode), and the second electrode of the second pair of electrodes is positioned along a second equipotential line extending from the location of minimum electrical potential. The first and the second subcutaneous devices measure a first and a second cardiac electrical signal. The first cardiac electrical signal represents an electrical potential between the first and the second electrode of the first pair of electrodes, and the second cardiac electrical signal represents an electrical potential between the first and the second electrode of the second pair of electrodes. The first and the second cardiac electrical signals are stored in a memory of the respective first and second subcutaneous devices and are transmitted to an external device (i.e., a device that has not been subcutaneously implanted) when requested to do so by the external device. In some embodiments, the external device is a device that a patient uses to draw cardiac electrical data from the implanted devices and to transmit such data to a separate device at a clinic. In some embodiments, the external device is a device at a clinic that receives cardiac electrical data from a patient device (or from the implanted devices themselves). The external device is configured for computing an enhanced cardiac electrical signal that represents a larger electrical potential difference than would be provided by either of the first or second subcutaneous devices alone. In accordance with an embodiment of the invention, the enhanced cardiac electrical signal is also computed as a linear or nonlinear combination of the first and the second cardiac electrical signals (e.g., an arithmetic sum of such signals) by way of a synchronization mechanism.

A method, in accordance with an embodiment of the invention, includes adding a second, third or more ECG devices. This can include recommending implantation of a supplemental subcutaneous device (e.g., when it is determined that the received cardiac electrical data does not enable a physician to identify the cardiac event that prompted the patient to request the data from the implanted device(s)). This could be because the electrodes of the existing ECG device(s) are not positioned properly to provide accurate cardiac electrical data regarding the first predetermined ECG signal. This could be because the cardiac electrical data regarding the first predetermined ECG signal, though accurately provided, does not provide sufficient diagnostic information explain the cardiac event. Adding a supplemental ECG device can address any inaccuracies or insufficiencies in electrode positioning and/or position electrodes to gather information regarding a second (or subsequent) predetermined ECG signal.

Generally, embodiments of the present invention pertain to generating an enhanced cardiac electrical signal by combining the cardiac electrical signals measured by at least two ECG devices. In some embodiments, one or more of the ECG devices can be external (e.g., to provide increased simplicity, ease of implementation, convenience, etc.). In preferred embodiments, the ECG devices can be subcutaneous. Some particularly advantageous embodiments are able to accommodate the decreasing size of subcutaneous devices for monitoring cardiac electrical activity.

The component that computes the enhanced cardiac electrical signal can vary in different embodiments. For example, in some embodiments, the first ECG device can provide the first cardiac electrical signal to an external device, and the second ECG device can also provide the second cardiac electrical signal to the external device, which can compute the enhanced cardiac electrical signal. In another example, the first ECG device can provide the first cardiac electrical signal to the second ECG device, and the second ECG device can provide both the first and second cardiac electrical signals to an external device, which can compute the enhanced cardiac electrical signal. In yet another example, the first ECG device can provide the first cardiac electrical signal to the second ECG device, and the second ECG device can compute the enhanced cardiac electrical signal.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
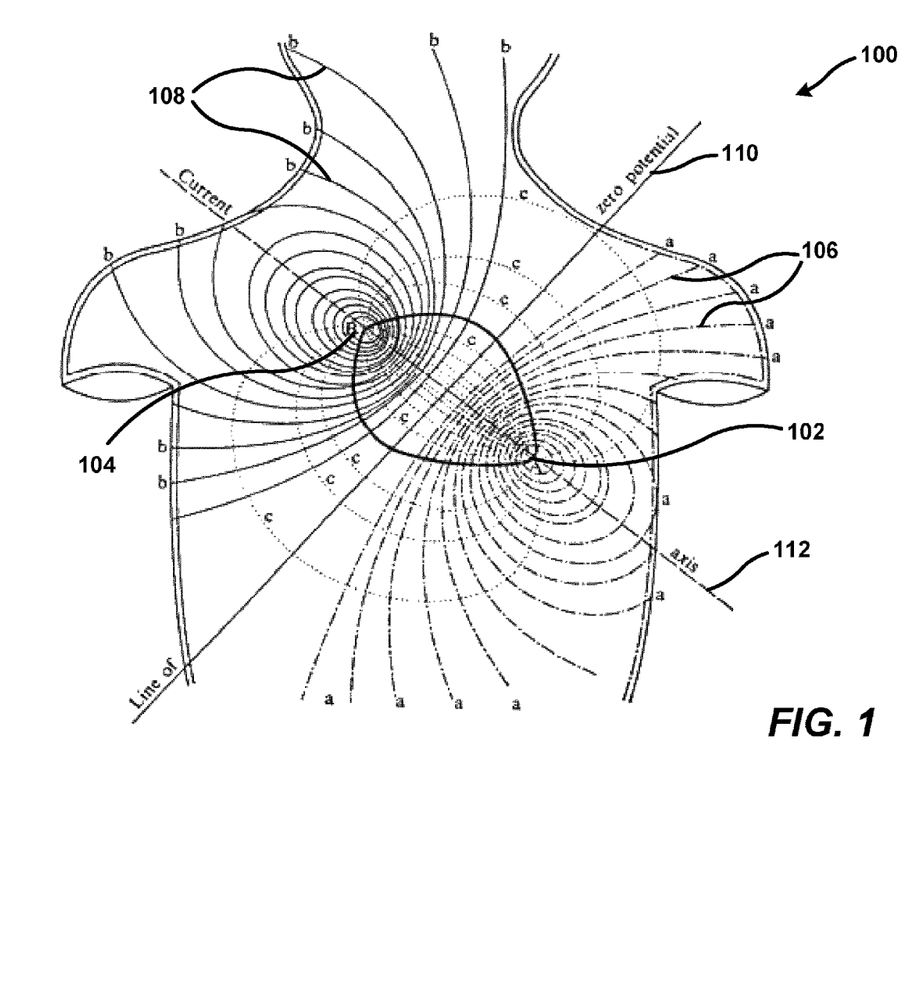
FIG. 1 is an illustration of a body surface potential map.

FIG. 1 is an illustration of a body surface potential map 100 on a human chest in accordance with a dipolar model of a cardiac current generator. As shown, potential map 100 includes location 102 of maximum electrical potential and location 104 of minimum electrical potential. The change in electrical potential from one of maximum electrical potential at location 102 to one of minimum electrical potential at location 104 is represented by equipotential lines 106 and 108, also labeled as "a" and "b", respectively. The potential change or voltage between point 102 and any point on one of the equipotential lines 106 is the same. As equipotential lines 106 and 108 extend from locations 102 and 104 of maximum and minimum electrical potential, respectively, there exists a "line of zero potential" 110. Additionally, the difference in the electrical potential between locations 102 and 104 of maximum and minimum electrical potential, respectively, results in the largest potential change or voltage between any two locations on the patient's torso.

Figure 2:
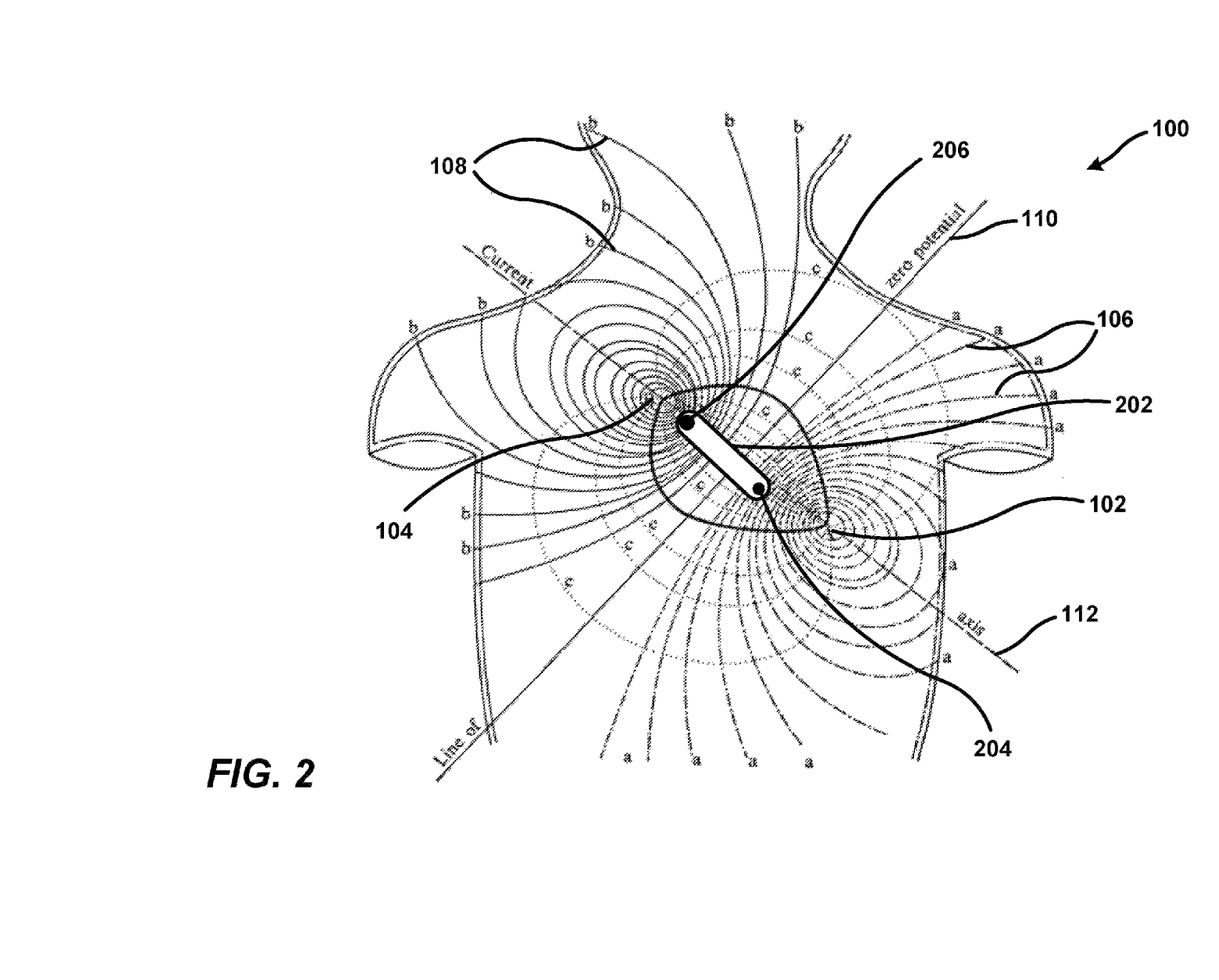
FIG. 2 is an illustration of a prior art subcutaneous device for monitoring cardiac electrical signals.

FIG. 2 illustrates the location or positioning of an subcutaneous device 202 for monitoring cardiac electrical activity of a patient. In FIG. 2, subcutaneous device 202 is shown superimposed on the body surface potential map 100. Subcutaneous device 202 comprises a pair of electrodes 204 and 206 positioned near longitudinally opposing ends of subcutaneous device 202. In accordance with methods well known in the art for implanting a cardiac monitoring device, each electrode 204 and 206 of the pair of electrodes of subcutaneous device 202 is respectively positioned generally near locations 102 and 104 of maximum and minimum electrical potential. In this way, the difference in measured potential between electrode 204 and electrode 206 can provide important information about the body surface potential map 100 and the patient's cardiac condition.

Because prior art devices such as device 202 are implanted subcutaneously in a patient, it is desirable to make such devices as small as possible for ease of surgically implanting and/or replacing the device with minimally invasive procedures, and also for lending comfort to the patient after the device has been implanted. However, in order to robustly monitor and record cardiac electrical activity, it is highly desirable to have a large ECG signal, preferably with electrodes placed at the maximum and minimum electrical potentials at locations 102 and 104, respectively. As can be seen, decreasing the length of a device such as subcutaneous devices 202 will also decrease the longitudinal distance between electrodes 204 and 206, thereby decreasing the amplitude of the ECG signal. Accordingly, the cardiac electrical activity monitored and/or recorded by such a smaller device may not be sufficiently robust or meaningful for diagnosis purposes. Furthermore, smaller devices provide less margin for error in placement, with any mis-alignment or incorrect placement of any one or both electrodes 204 and 206 being further magnified and potentially resulting in cardiac electrical data that is not sufficiently robust or meaningful for diagnosis purposes.

These and other shortcomings of prior art devices such as subcutaneous device 202 and/or implantable cardiac monitoring devices smaller than prior art devices are addressed by embodiments of the instant invention.

Figure 3:
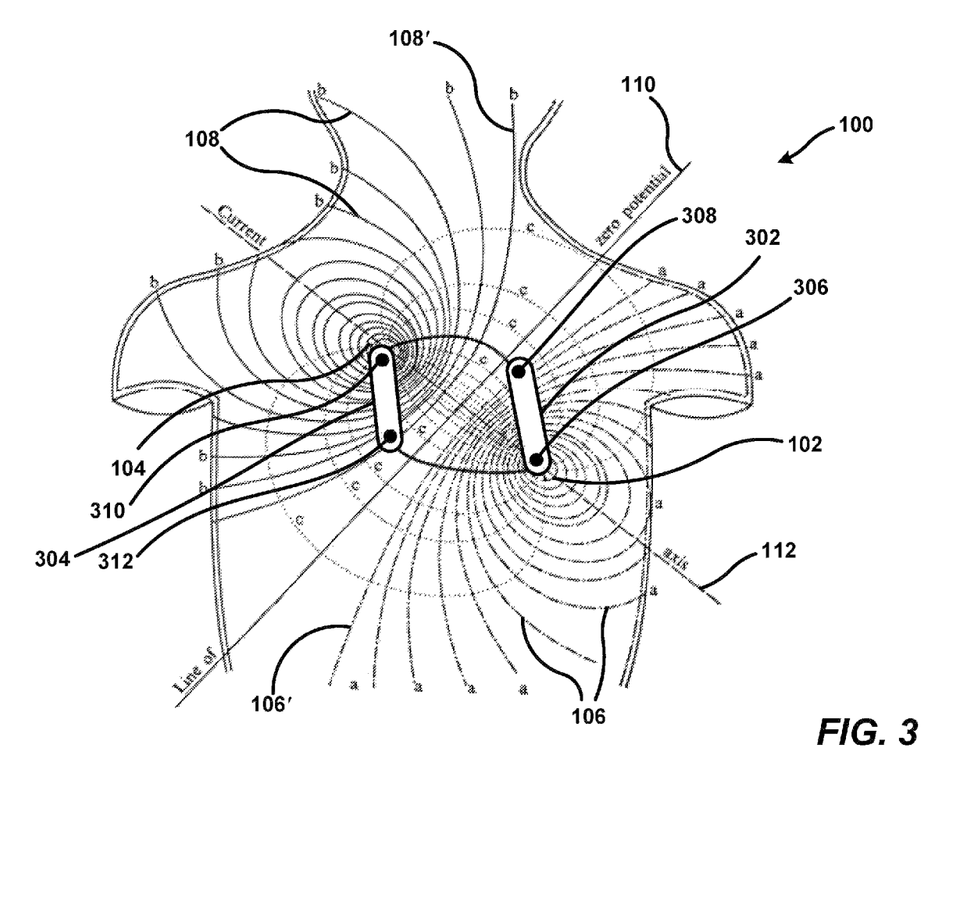
FIG. 3 is an illustration of at least two subcutaneous devices for enhancing cardiac electrical signals.

FIG. 3 illustrates the location or positioning of at least two subcutaneous devices 302 and 304 for monitoring and/or recording cardiac electrical activity, wherein each one of the two devices 302 and 304 is smaller than prior art devices such as subcutaneous device 202 of FIG. 2. In FIG. 3, the two subcutaneous devices 302 and 304 are shown superimposed on the body surface potential map 100. First subcutaneous device 302 comprises a first pair of electrodes 306 and 308 positioned near longitudinally opposing ends of first subcutaneous device 302. As shown, first subcutaneous device 302 is implanted such that first electrode 306 of the first pair of electrodes is positioned near location 102 of maximum electrical potential for a first predetermined ECG signal (relative to second electrode 308). Also as shown, second electrode 308 of the first pair of electrodes is positioned along a first equipotential line 106' extending from location 102 of maximum electrical potential for the first predetermined ECG signal. As such, first subcutaneous device 302 will provide a first cardiac electrical signal measured as the electrical potential between its electrodes 306 and 308. Similarly, second subcutaneous device 304 comprises a second pair of electrodes 310 and 312 positioned near longitudinally opposing ends of second subcutaneous device 304. As shown, second subcutaneous device 304 is implanted such that first electrode 310 of the second pair of electrodes is positioned near location 104 of minimum electrical potential for the first predetermined ECG signal (relative to second electrode 312). Also as shown, second electrode 312 of the second pair of electrodes is positioned along a second equipotential line 108' extending from location 104 of minimum electrical potential for the first predetermined ECG signal. As such, second subcutaneous device 304 will provide a second cardiac electrical signal measured as the electrical potential between its electrodes 310 and 312. Then, as is discussed in greater detail below, in accordance with an embodiment of the invention, an enhanced cardiac electrical signal is computed as a linear or nonlinear combination of the first and the second cardiac electrical signals (e.g., an arithmetic sum of such signals). A synchronization mechanism can be provided between the two subcutaneous devices 302 and 304 to enable combination of the signals.

Also in accordance with an embodiment of the invention, an external device requests and receives the first and the second cardiac electrical signals, respectively, from the first and the second subcutaneous devices 302 and 304. This sequence is often initiated by a patient who has just experienced a cardiac event. He/she then typically instructs the external device to make such a request of the implanted devices. The external device then transmits the first and the second cardiac electrical signals it received from the first and the second subcutaneous devices 302 and 304, respectively, (in raw form or after processing) to another device (e.g., located at a clinic) which is configured for computing an enhanced cardiac electrical signal. In many such embodiments, the enhanced cardiac electrical signal represents a difference in electrical potential that is greater than the electrical potential difference between electrodes 306 and 308 or between electrodes 306 and 308.

The initial request for the cardiac electrical signal(s) from the device(s) can come from a several sources. For example, as alluded to above, the patient can initiate the request (e.g., while or after experiencing a cardiac event). In another example, the request can be initiated automatically according to a predetermined schedule of time intervals. In yet another example, the request can be initiated automatically by a diagnostic algorithm.

In an embodiment of the invention, first subcutaneous device 302 is configured for measuring a plurality of the first cardiac electrical signals over a pre-specified period of time and storing the measured plurality of the first cardiac electrical signals in a memory of the first subcutaneous device 302. Similarly, second subcutaneous device 304 is configured for measuring a plurality of the second cardiac electrical signals over a pre-specified period of time and storing the measured plurality of the second cardiac electrical signals in a memory of the second subcutaneous device 304. The plurality of the first and the second cardiac electrical signals respectively stored in the memory of the first and the second subcutaneous devices 302 and 304 are transmitted to the external device upon receiving a request from the external device.

In an embodiment of the invention, the plurality of the first cardiac electrical signals measured by the first subcutaneous device 302 span a first period of time encompassing a pre-specified period of time both before and after receiving the request, from the external device, to transmit the plurality of the first cardiac electrical signals. Similarly, the plurality of the second cardiac electrical signals measured by the second subcutaneous device 304 span a first period of time encompassing a pre-specified period of time both before and after receiving the request, from the external device, to transmit the plurality of the second cardiac electrical signals. In this way, when a patient experiences a cardiac event, he/she can initiate transmission of cardiac electrical data to a clinic device for analysis, and the transmitted data can be from just before the cardiac event and just after the cardiac event, thereby giving the physician a clear picture of the predetermined ECG signal throughout the cardiac event.

As described in the foregoing, the enhanced cardiac electrical signal, in an embodiment of the invention, is computed as an arithmetic sum (or other a linear or nonlinear combination) of the first cardiac electrical signal and the second cardiac electrical signal. Also as described in the foregoing, and also in accordance with an embodiment of the invention, the first cardiac electrical signal is measured by the first subcutaneous device 302 as the difference in the electrical potential between its corresponding first and second electrodes 306 and 308 of the first pair of electrodes. Similarly, the second cardiac electrical signal is measured by the second subcutaneous device 304 as the difference in the electrical potential between its corresponding first and second electrodes 310 and 312 of the second pair of electrodes. For example, if $V_{306}$ and $V_{308}$, respectively, are the electrical potentials measured by the first and the second electrodes 306 and 308 of the first pair of electrodes of the first subcutaneous device 302, then the first cardiac electrical signal measured by the first subcutaneous device 302 is $V_{302}=V_{306}-V_{308}$. Similarly, if $V_{310}$ and $V_{312}$, respectively, are the electrical potentials measured by the first and the second electrodes 310 and 312 of the second pair of electrodes of the second subcutaneous device 304, then the second cardiac electrical signal measured by the second subcutaneous device 304 is $V_{304}=V_{312}-V_{310}$. Accordingly, in some embodiments, the enhanced cardiac electrical signal between the locations 102 and 104 of maximum and minimum potentials, respectively, can be computed as $$V_{EN}=V_{302}+V_{304}=(V_{306}-V_{308})+(V_{312}-V_{310})=V_{306}-V_{308}+V_{312}-V_{310}$$

As can be seen, by locating the second electrode 308 of the first pair of electrodes of the first subcutaneous device 302 on an equipotential line that is near the equipotential line of the second electrode 312 of the second pair of electrodes of the second subcutaneous device 304, the electrical potentials $V_{308}$ and $V_{312}$ will be very similar or essentially equal. Accordingly, $V_{EN}=V_{306}-V_{310}$. In some instances in which the first electrode 306 of the first pair of electrodes of the first subcutaneous device 302 is positioned proximate the location 102 of maximum potential, the electrical potential $V_{306}$ can approximate the maximum potential. Similarly, in instances in which the first electrode 310 of the second pair of electrodes of the second subcutaneous device 304 is positioned proximate the location 104 of minimum potential, the electrical potential $V_{310}$ can approximate the minimum potential. Therefore, in such instances in which the enhanced cardiac electrical signal $V_{EN}$ is computed as an arithmetic sum of the first cardiac electrical signal $V_{302}$ measured by the first subcutaneous device 302 and the second cardiac electrical signal $V_{304}$ measured by the second subcutaneous device 304, the enhanced cardiac electrical signal can approximate the difference in electrical potential between the locations 102 and 104 of maximum and minimum potentials, respectively.

As described in the foregoing, there exists a "line of zero potential" 110 between the locations 102 and 104 of maximum and minimum electrical potential. Accordingly, by locating both second electrodes 308 and 312 of the first and the second pair of electrodes of the first and the second subcutaneous devices 302 and 304 substantially near the "line of zero potential" 110, the electrical potentials $V_{308}$ and $V_{312}$ can be essentially negligible, and therefore, the enhanced cardiac electrical signal $V_{EN}=V_{306}-V_{310}$.

In some embodiments of the invention, an external device (e.g., located at a clinic) requests and receives the first and the second cardiac electrical signals, respectively, from the first and the second subcutaneous devices 302 and 304. The external device then computes an enhanced cardiac electrical signal.

Figure 4:
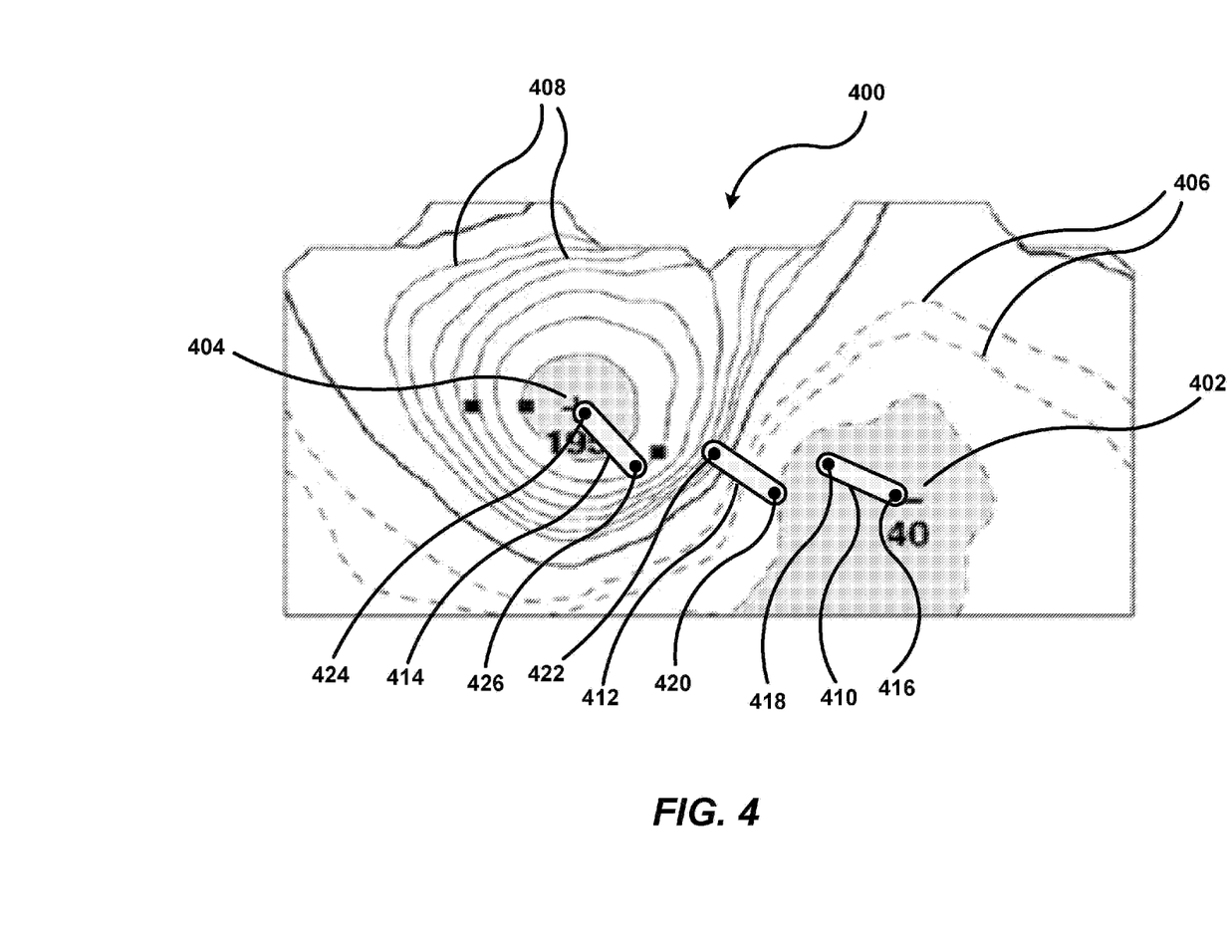
FIG. 4 is an illustration of at least three subcutaneous devices for enhancing cardiac electrical signals.

FIG. 4 is an illustration of a body surface potential map 400 on a human chest in accordance with a dipolar model of a cardiac current generator (found in Horacek et al., *Optimal Electrocardiographic Leads for Detecting Acute Myocardial Ischemia*, 34 Journal of Electrocardiology 97 (2001)). As shown, potential map 400 includes location 402 of maximum electrical potential and location 404 of minimum electrical potential for a predetermined ECG signal. The change in electrical potential from one of maximum electrical potential at location 402 to one of minimum electrical potential at location 404 is represented by equipotential lines 406 and 408, respectively. In accordance with an embodiment of the invention, FIG. 4 illustrates the location or positioning of at least three subcutaneous devices 410, 412 and 414 for monitoring and/or recording cardiac electrical activity, wherein each one of the three subcutaneous devices 410, 412 and 414 are smaller than the prior art devices such as subcutaneous device 202. First subcutaneous device 410 comprises a first pair of electrodes 416 and 418 positioned near longitudinally opposing ends of first subcutaneous device 410. As shown, first subcutaneous device 410 is implanted such that first electrode 416 of the first pair of electrodes is positioned near location 402 of maximum electrical potential for a first predetermined ECG signal (relative to the second electrode 418). Also, second electrode 418 of the first pair of electrodes can be positioned along an equipotential line (not shown) extending from location 402 of maximum electrical potential for the first predetermined ECG signal. As such, first subcutaneous device 410 will provide a first cardiac electrical signal measured as the electrical potential between its electrodes 416 and 418. Similarly, second subcutaneous device 412 comprises a second pair of electrodes 420 and 422 positioned near longitudinally opposing ends of second subcutaneous device 412. As shown, second subcutaneous device 412 is implanted such that first electrode 420 of the second pair of electrodes is positioned near equipotential line 406 for the first predetermined ECG signal. Also as shown, second electrode 422 of the second pair of electrodes is positioned along equipotential line 408 extending from location 404 of minimum electrical potential for the first predetermined ECG signal. As such, second subcutaneous device 412 will provide a second cardiac electrical signal measured as the electrical potential between its electrodes 420 and 422. Also, third subcutaneous device 414 comprises a third pair of electrodes 424 and 426 positioned near longitudinally opposing ends of third subcutaneous device 414. As shown, third subcutaneous device 414 is implanted such that first electrode 424 of the third pair of electrodes is positioned near location 404 of minimum electrical potential for a second predetermined ECG signal (relative to the second electrode 426). Also as shown, second electrode 426 of the third pair of electrodes is positioned near equipotential line 408 extending from location 404 of minimum electrical potential for the second predetermined ECG signal. As such, third subcutaneous device 414 will provide a third cardiac electrical signal measured as the electrical potential between its electrodes 424 and 426.

As described in the foregoing with reference to FIG. 3, the external device can request and receive the third cardiac electrical signal from the third subcutaneous device 414 in addition to the first and the second cardiac electrical signals from the first and the second subcutaneous devices 410 and 412. The external device then transmits the first, the second and the third cardiac electrical signals it received from the first, the second and the third subcutaneous devices 410, 412 and 414, respectively, to another device which is configured for computing an enhanced cardiac electrical signal. The enhanced cardiac electrical signal can be an arithmetic sum (or other linear or nonlinear combination) of the first, second, and third cardiac electrical signals. This can be especially effective in approximating the potential difference between location 402 and location 404 if electrode 418 and electrode 420 are on similar (or the same) equipotential lines and if electrode 426 and electrode 422 are on similar (or the same) equipotential lines.

As with embodiments discussed above, the request for the cardiac electrical signals can be made by an external device located near the patient or at a clinic. One or more external devices can then compute the enhanced cardiac electrical signal.

As previously described, a mis-alignment or incorrect placement of any one or both electrodes of a pair of electrodes of one or more ECG devices can result in cardiac electrical data that is not sufficiently robust or meaningful for diagnosis purposes. Also, it may be determined that the one or more ECG devices already installed are inadequate for providing cardiac electrical data for a specific ECG signal and/or cardiac event or for a different ECG signal and/or cardiac event than initially desired. Accordingly, it may be desirable to add a supplemental ECG device for enhancing the cardiac electrical signals.

Figure 5:
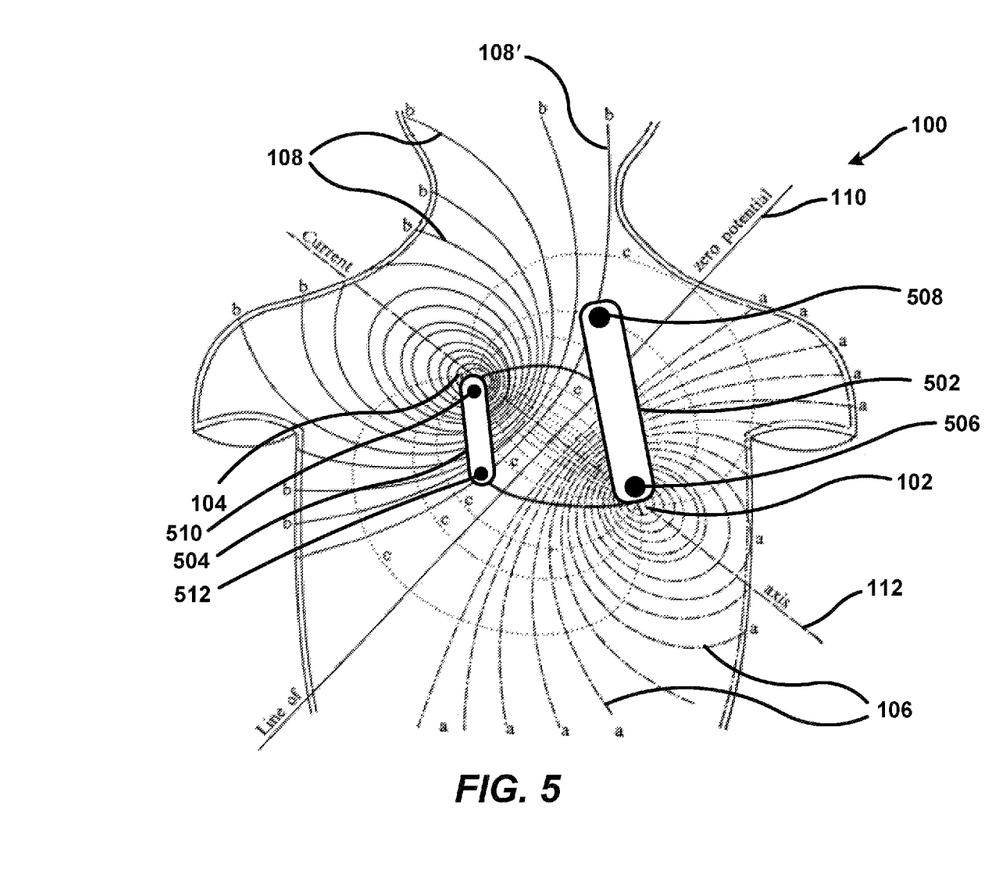
FIG. 5 is an illustration of a supplemental subcutaneous device implanted for enhancing cardiac electrical signals.

One such embodiment is illustrated in FIG. 5 wherein the two subcutaneous devices 502 and 504 are shown superimposed on the body surface potential map 100. First subcutaneous device 502 comprises a first pair of electrodes 506 and 508 positioned near longitudinally opposing ends of first subcutaneous device 502. As shown, first subcutaneous device 502 is implanted such that first electrode 506 of the first pair of electrodes is positioned near location 102 of maximum electrical potential for a first predetermined ECG signal (relative to the second electrode 508). Also as shown, second electrode 508 of the first pair of electrodes is positioned along equipotential line 108' extending from location 104 of minimum electrical potential for the first predetermined ECG signal. As such, first subcutaneous device 502 will provide a first cardiac electrical signal measured as the electrical potential between its electrodes 506 and 508. Upon reviewing the first cardiac electrical signal from the first subcutaneous device 502, a care giver may conclude that first subcutaneous device 502 is not correctly positioned for the first predetermined ECG signal or not able to provide adequate diagnostic information and may accordingly recommend the implantation of supplemental subcutaneous device 504. As with subcutaneous device 502, supplemental subcutaneous device 504 comprises a supplemental pair of electrodes 510 and 512 positioned near longitudinally opposing ends of supplemental subcutaneous device 504. As shown, supplemental subcutaneous device 504 is implanted such that first electrode 510 of the supplemental pair of electrodes is positioned near location 104 of minimum electrical potential for the first predetermined ECG signal (relative to the second electrode 512). Also as shown, second electrode 512 of the supplemental pair of electrodes is positioned along equipotential line 108' extending from location 104 of minimum electrical potential for the first predetermined ECG signal. As such, supplemental subcutaneous device 504 will provide a supplemental cardiac electrical signal measured as the electrical potential between its electrodes 510 and 512. Then, because the electrical potential difference between electrode 512 and electrode 508 is essentially negligible, an enhanced cardiac electrical signal can be computed as an arithmetic sum (or other linear or nonlinear combination) of the first cardiac electrical signal and the supplemental cardiac electrical signal, and the enhanced cardiac electrical signal can represent an electrical potential difference that is greater than the electrical potential difference between electrodes 506 and 508 or electrodes 510 and 512.

Figure 6:
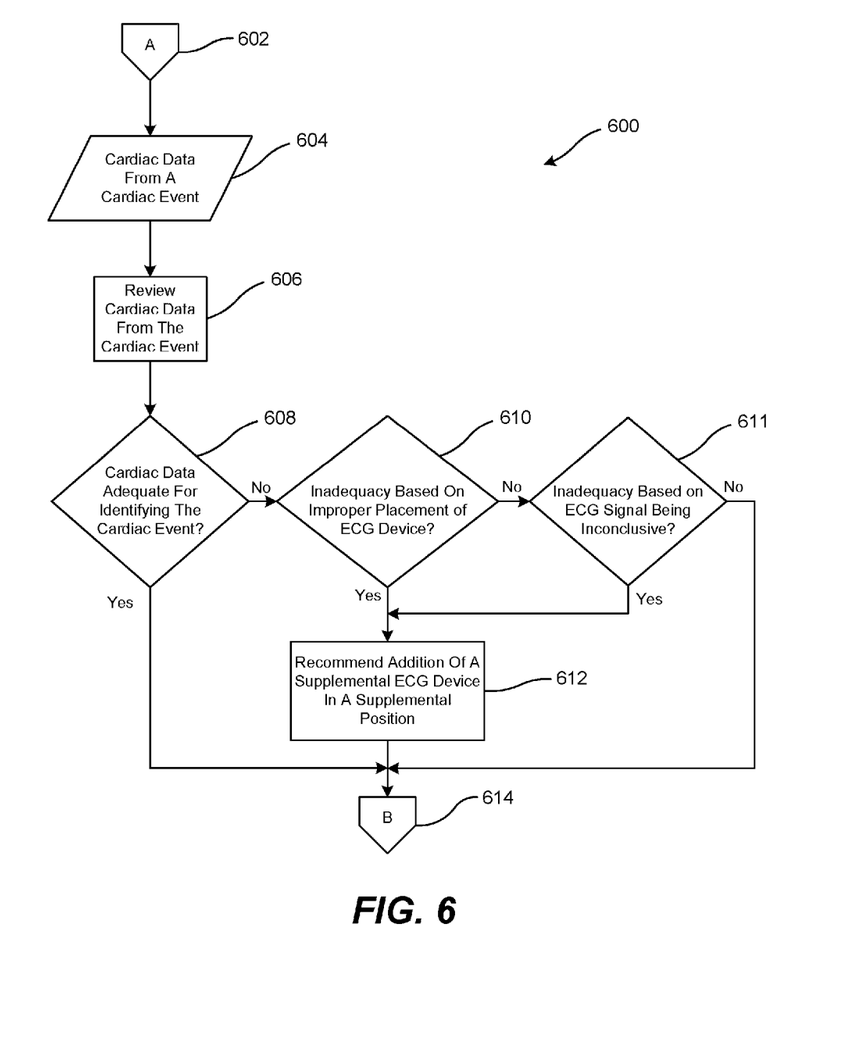
FIG. 6 is a flowchart of a method for adding a supplemental ECG device for enhancing cardiac electrical signals.

FIG. 6 is a flowchart 600 of a method for recommending addition of a supplemental ECG device (e.g., a subcutaneous device) when it is determined that the cardiac data provided by one or more existing devices does not provide adequate information regarding the patient's cardiac event. For example, the existing device(s) can be improperly positioned for providing accurate cardiac electrical data regarding a first predetermined ECG signal. In another example, it can be determined that the first predetermined ECG signal does not completely explain the patient's event, so monitoring a different/additional ECG signal can be recommended. For example, the existing device(s) can be positioned for monitoring arrhythmia, and a supplemental ECG device can be recommended for monitoring for coronary artery disease (either in addition to arrhythmia or instead of arrhythmia). As shown, the illustrative method begins at 602 wherein at block 604 the cardiac data relating to a cardiac event as represented by a first predetermined ECG signal is made available (e.g., according to one of the ways set forth elsewhere herein). The cardiac data from block 604 is reviewed by the care giver at block 606. Then, at block 608 the care giver makes a determination whether or not the cardiac data from block 604 is adequate for identifying the cardiac event of interest. If the cardiac data from block 604 is determined to be adequate, then the method proceeds to end block 614. If the cardiac data from block 604 is determined to be inadequate, then the method proceeds to block 610. At block 610, a determination is made about whether the inadequacy of the cardiac data is based on improper positioning of the existing device(s). If the inadequacy of the cardiac data is based on improper positioning of the existing device(s), the method proceeds to block 612 (which is discussed below). If the inadequacy of the cardiac data is not based on improper positioning of the existing device(s), the method proceeds to block 611. At block 611, a determination is made about whether the inadequacy of the cardiac data is based on the first predetermined ECG signal being inconclusive of the patient's cardiac event. If the inadequacy of the cardiac data is based on the first predetermined ECG signal being inconclusive of the patient's cardiac event, the method proceeds to block 612 (which is discussed below). If the inadequacy of the cardiac data is not based on the first predetermined ECG device being inconclusive of the patient's cardiac event, the method proceeds to block 614.

As noted, if the cardiac data is inadequate for identifying or addressing the patient's cardiac event because of improper placement of the existing device or because the ECG signal is inconclusive, the method proceeds to block 612. At block 612, the care giver recommends addition of a supplemental ECG device (e.g., subcutaneously implanted). The supplemental ECG device can have similar characteristics as ECG devices discussed elsewhere herein. Addition of the supplemental ECG device can address the improper placement of the existing device as discussed elsewhere herein. Addition of the supplemental ECG device can involve positioning the supplemental ECG device in an optimal location for monitoring a different ECG signal.

Thus, embodiments of the invention are disclosed. Although the present invention has been described in considerable detail with reference to certain disclosed embodiments, the disclosed embodiments are presented for purposes of illustration and not limitation and other embodiments of the invention are possible. For example, though the inventive concepts discussed herein have been described in connection with subcutaneous devices, it should be appreciated that many of the concepts can be implemented with cutaneous devices, as well as with combinations of cutaneous and subcutaneous devices. One skilled in the art will appreciate that various changes, adaptations, and modifications may be made without departing from the spirit of the invention and the scope of the appended claims.

What is claimed is:

1. A method of monitoring cardiac electrical activity, comprising:
   requesting a first cardiac electrical signal from a first ECG device, the first ECG device comprising a first pair of electrodes positioned on longitudinally opposing ends of said first ECG device, wherein
      a first electrode of the first pair of electrodes is positioned at a location of maximum electrical potential for a first predetermined ECG signal; and
      a second electrode of the first pair of electrodes is positioned along a first equipotential line extending from the location of maximum electrical potential for the first predetermined ECG signal;
   receiving the first cardiac electrical signal;
   requesting a second cardiac electrical signal from a second ECG device, the second ECG device comprising a second pair of electrodes positioned on longitudinally opposing ends of said second ECG device, wherein
      a first electrode of the second pair of electrodes is positioned at a location of minimum electrical potential for the first predetermined ECG signal; and
      a second electrode of the second pair of electrodes is positioned along a second equipotential line extending from the location of minimum electrical potential for the first predetermined ECG signal;
   receiving the second cardiac electrical signal; and
   computing an enhanced cardiac electrical signal based on the first and second cardiac signals, the enhanced cardiac electrical signal representing a larger electrical potential difference than either the electrical potential difference between the first pair of electrodes or the electrical potential difference between the second pair of electrodes.

2. The method of claim 1, wherein
   the first pair of electrodes measures an arithmetic difference in an electrical potential between the first and the second electrode of the first pair of electrodes;
   the second pair of electrodes measures an arithmetic difference in an electrical potential between the first and the second electrode of the second pair of electrodes; and
   the enhanced cardiac electrical signal is an arithmetic sum of the first cardiac electrical signal and the second cardiac electrical signal.

3. The method of claim 1, wherein the first and second ECG devices are both implanted subcutaneously in a patient.

4. The method of claim 1, wherein an arithmetic difference in an electrical potential between the second electrode of the first ECG device and the second electrode of the second ECG device is essentially negligible.

5. The method of claim 1, further comprising
   requesting a third cardiac electrical signal from a third ECG device, the third ECG device comprising a third pair of electrodes positioned on longitudinally opposing ends of said third ECG device, wherein
      a first electrode of the third pair of electrodes is positioned at a location of either maximum or minimum electrical potential for a second predetermined ECG signal; and
      a second electrode of the third pair of electrodes is positioned along a third equipotential line extending from the location of either maximum or minimum electrical potential for the second predetermined ECG signal;
   receiving the third cardiac electrical signal; and
   computing a second enhanced cardiac electrical signal based on the first or second cardiac electrical signal and the third cardiac electrical signal, the second enhanced cardiac electrical signal representing a larger electrical potential difference than either the electrical potential difference between the first or second pair of electrodes or the electrical potential difference between the third pair of electrodes.

6. A method of monitoring cardiac electrical activity, comprising:
   requesting a first cardiac electrical signal from a first ECG device, the first ECG device comprising a first pair of electrodes positioned on longitudinally opposing ends of said first ECG device, wherein a first electrode of the first pair of electrodes is positioned at a location of maximum electrical potential for a first predetermined ECG signal; and a second electrode of the first pair of electrodes is positioned along a first equipotential line extending from the location of maximum electrical potential for the first predetermined ECG signal;

receiving the first cardiac electrical signal;

requesting a second cardiac electrical signal from a second ECG device, the second ECG device comprising a second pair of electrodes positioned on longitudinally opposing ends of said second ECG device, wherein a first electrode of the second pair of electrodes is positioned at a location of minimum electrical potential for the first predetermined ECG signal; and a second electrode of the second pair of electrodes is positioned along a second equipotential line extending from the location of minimum electrical potential for the first predetermined ECG signal;

receiving the second cardiac electrical signal; and computing an enhanced cardiac electrical signal based on the first and second cardiac signals, the enhanced cardiac electrical signal representing a larger electrical potential difference than either the electrical potential difference between the first pair of electrodes or the electrical potential difference between the second pair of electrodes; and wherein the first and second ECG devices are both implanted subcutaneously in a patient; and the first ECG device is configured for measuring a plurality of the first cardiac electrical signal over a pre-specified period of time; and storing the plurality of the first cardiac electrical signal in a memory of the first ECG device;

the second ECG device is configured for measuring a plurality of the second cardiac electrical signal over a pre-specified period of time; and storing the plurality of the second cardiac electrical signal in a memory of the second ECG device;

requesting the first cardiac electrical signal from said first ECG device comprises requesting the plurality of the first cardiac electrical signal;

receiving the first cardiac electrical signal comprises receiving the plurality of the first cardiac electrical signal from the first ECG device;

requesting the second cardiac electrical signal from said second ECG device comprises requesting the plurality of the second cardiac electrical signal; and receiving the second cardiac electrical signal comprises receiving the plurality of the second cardiac electrical signal from the second ECG device.

7. The method of claim 6, wherein said plurality of the first cardiac electrical signal received from the first ECG device comprises said plurality of the first cardiac electrical signal for a first period of time, said first period of time including time before and after receiving said request for the plurality of the first cardiac electrical signal; and plurality of the second cardiac electrical signal received from the second ECG device comprises said plurality of the second cardiac electrical signal for a second period of time, said second period of time including time before and after receiving said request for the plurality of the second cardiac electrical signal.

8. The method of claim 6, wherein the plurality of the first cardiac electrical signal and the plurality of the second cardiac electrical signal each span a plurality of cardiac cycles.

9. A method of monitoring cardiac electrical activity, comprising receiving a first cardiac electrical signal, the first cardiac electrical signal being from a first ECG device, said first ECG device comprising a first pair of electrodes positioned on longitudinally opposing ends of said first ECG device, wherein a first electrode of the first pair of electrodes is positioned at a location of maximum electrical potential for a first predetermined ECG signal; and a second electrode of the first pair of electrodes is positioned along a first equipotential line extending from the location of maximum electrical potential for the first predetermined ECG signal;

receiving a second cardiac electrical signal, the second cardiac electrical signal being from a second ECG device, said second ECG device comprising a second pair of electrodes positioned on longitudinally opposing ends of said second ECG device, wherein a first electrode of the second pair of electrodes is positioned at a location of minimum electrical potential for the first predetermined ECG signal; and a second electrode of the second pair of electrodes is positioned along a second equipotential line extending from the location of minimum electrical potential for the first predetermined ECG signal; and computing a first enhanced cardiac electrical signal based on the first and second cardiac electrical signals, the first enhanced cardiac electrical signal representing a larger electrical potential difference than either the electrical potential difference between the first pair of electrodes or the electrical potential difference between the second pair of electrodes.

10. The method of claim 9, wherein the first pair of electrodes measures an arithmetic difference in an electrical potential between the first and the second electrode of the first pair of electrodes;

the second pair of electrodes measures an arithmetic difference in an electrical potential between the first and the second electrode of the second pair of electrodes; and the first enhanced cardiac electrical signal is an arithmetic sum of the first cardiac electrical signal and the second cardiac electrical signal.

11. The method of claim 9, wherein an arithmetic difference in an electrical potential between the second electrode of the first ECG device and the second electrode of the second ECG device is essentially negligible.

12. The method of claim 9, further comprising receiving a third cardiac electrical signal from a third ECG device, the third ECG device comprising a third pair of electrodes positioned on longitudinally opposing ends of said third ECG device, wherein a first electrode of the third pair of electrodes is positioned at a location of either maximum or minimum electrical potential for a second predetermined ECG signal; and a second electrode of the third pair of electrodes is positioned along a third equipotential line extending from the location of either maximum or minimum electrical potential for the second predetermined ECG signal; and computing a second enhanced cardiac electrical signal based on the first or second cardiac electrical signal and the third cardiac electrical signal, the second enhanced cardiac electrical signal representing a larger electrical potential difference than either the electrical potential difference between the first or second pair of electrodes or the electrical potential difference between the third pair of electrodes.

13. A method of monitoring cardiac electrical activity, comprising receiving a first cardiac electrical signal, the first cardiac electrical signal being from a first ECG device, said first ECG device comprising a first pair of electrodes positioned on longitudinally opposing ends of said first ECG device, wherein
- a first electrode of the first pair of electrodes is positioned at a location of maximum electrical potential for a first predetermined ECG signal; and
- a second electrode of the first pair of electrodes is positioned along a first equipotential line extending from the location of maximum electrical potential for the first predetermined ECG signal;

receiving a second cardiac electrical signal, the second cardiac electrical signal being from a second ECG device, said second ECG device comprising a second pair of electrodes positioned on longitudinally opposing ends of said second ECG device, wherein
- a first electrode of the second pair of electrodes is positioned at a location of minimum electrical potential for the first predetermined ECG signal; and
- a second electrode of the second pair of electrodes is positioned along a second equipotential line extending from the location of minimum electrical potential for the first predetermined ECG signal; and computing a first enhanced cardiac electrical signal based on the first and second cardiac electrical signals, the first enhanced cardiac electrical signal representing a larger electrical potential difference than either the electrical potential difference between the first pair of electrodes or the electrical potential difference between the second pair of electrodes, wherein:

the first ECG device is configured for
measuring a plurality of the first cardiac electrical signal over a pre-specified period of time; and
storing the plurality of the first cardiac electrical signal in a memory of the first ECG device;
the second ECG device is configured for measuring a plurality of the second cardiac electrical signal over a pre-specified period of time; and
storing the plurality of the second cardiac electrical signal in a memory of the second ECG device;
receiving the first cardiac electrical signal comprises receiving the plurality of the first cardiac electrical signal, the plurality of the first cardiac electrical signal being from the memory of the first ECG device; and
receiving the second cardiac electrical signal comprises receiving the plurality of the second cardiac electrical signal, the plurality of the second cardiac electrical signal being from the memory of the second ECG device.

14. The method of claim 13, wherein said
plurality of the first cardiac electrical signal comprises said plurality of the first cardiac electrical signal for a first period of time, said first period of time including time before and after the plurality of the first cardiac electrical signal is requested; and
plurality of the second cardiac electrical signal comprises said plurality of the second cardiac electrical signal for a second period of time, said second period of time including time before and after the plurality of the second cardiac electrical signal is requested.

15. The method of claim 13, wherein the plurality of the first cardiac electrical signal and the plurality of the second cardiac electrical signal each span a plurality of cardiac cycles.

* * * * *